United States Patent [19]

Guilfoyle et al.

[11] Patent Number: 5,376,549

[45] Date of Patent: Dec. 27, 1994

[54] CLONING VECTOR

[75] Inventors: Richard A. Guilfoyle; Lloyd M. Smith, both of Madison, Wis.

[73] Assignee: Wisconsin Alumni Research Foundation, Madison, Wis.

[21] Appl. No.: 14,944

[22] Filed: Feb. 5, 1993

[51] Int. Cl.$^5$ ............................................. C12N 15/70
[52] U.S. Cl. ................... 435/320.1; 435/172.3
[58] Field of Search ........................ 435/320.1, 172.3

[56] References Cited

PUBLICATIONS

Studier et al. (1986) J. Mol. Biol. vol. 189:113–130.

Beck, et al., "Nucleotide Sequence And Genome Organization Of Filamentous Bacteriophages f1 and fd", *Gene*, 16:35–38, 1981.

Fitzgerald, et al., "Rapid Shotgun Cloning Utilizing The Two Base Recognition Endonuclease CviJI", *Nucl. Acids Res.*, vol. 20, 14:3753–3762, 1992.

Pierce, et al., "A Positive Selection Vector For Cloning High Molecular Weight DNA By The Bacteriophage P1 System: Improved Cloning Efficacy", *Proc. Natl. Acad. Sci. U.S.A.*, 89:2056–2060, 1992.

Fulford, et al., "Regulation Of Bacteriophage f1 DNA Replication", *J. Mol. Biol.*, 203:49–62, 1988.

Waye, et al., "EcoK Selection Vectors For Shotgun Cloning Into M13 And Deletion Mutagenesis", *Nucl. Acids. Res.*, vol. 13, 23:8561–8571, 1985.

*Primary Examiner*—Richard A. Schwartz
*Assistant Examiner*—Kathleen L. Choi
*Attorney, Agent, or Firm*—Quarles & Brady

[57] ABSTRACT

A vector comprising a filamentous phage sequence containing a first copy of filamentous phage gene X and other sequences necessary for the phage to propagate is disclosed. The vector also contains a second copy of filamentous phage gene X downstream from a promoter capable of promoting transcription in a bacterial host. In a preferred form of the present invention, the filamentous phage is M13 and the vector additionally includes a restriction endonuclease site located in such a manner as to substantially inactivate the second gene X when a DNA sequence is inserted into the restriction site.

6 Claims, 2 Drawing Sheets

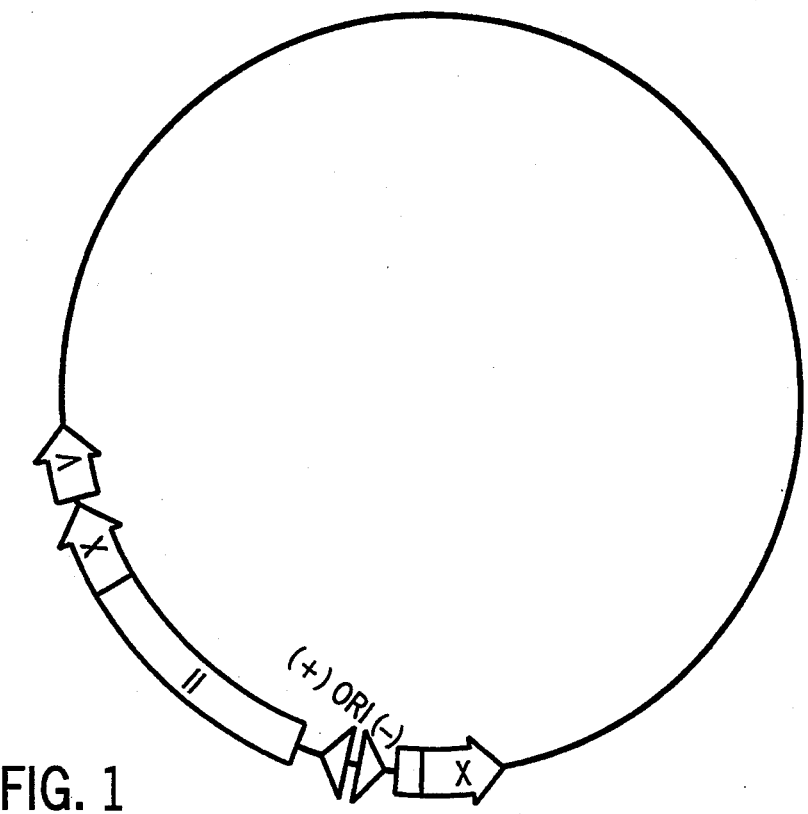
FIG. 1
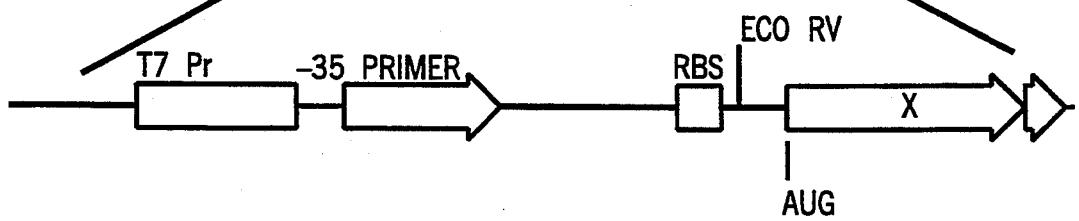

M13-100

```
                    T7PrL                    Promoter
GGATCCGATAGATCTCGACCCGCGAAATTAATACGACTCACTATA
Bam H1    Bgl II
                         -50 sp
GGGAGACCACAACGGTTTCCCTCTAGAAATAATTTTGTTTAACTTT
                              Xba I
     RBS           X----->
AAGAAGGAGATATCATATGAATATTTATGACGATTCCGCAGTATTG
         Eco RV

ACGCTATCCAGTCTAAACATTTTACTATTACCCCCTCTGGCAAAACTT

CTTTTGCAAAAGCCTCTCGCTATTTTGGTTTTTATCGTCGTCTGGTAAA

CGAGGGTTATGATAGTGTTGCTCTTACTATGCCTCGTAATTCCTTTTG

GCGTTATGTATCTGCATTAGTTGAATGTGGTATTCCTAAATCTCAACT

GATGAATCTTTCTACCTGTAATAATGTTGTTCCGTTAGTTCGTTTTAT

TAACGTAGATTTTTCTTCCCAACGTCCTGACTGGTATAATGAGCCAGT

TCTTAAAATCGCATAAATCGAATTC
                Eco R1
```

FIG. 2

CLONING VECTOR

This invention was made with United States Government support awarded by the Department of Energy (DOE), Grant No. DE FG02-90-ER61026. The United States Government has certain rights in this invention.

FIELD OF THE INVENTION

In general, the present invention relates to cloning vectors. Specifically, the present invention relates to filamentous phage cloning vectors that provide a direct selection mechanism for recombinant vectors.

BACKGROUND

The most widely used strategy for determining the sequence of a fairly large segment of cloned DNA is to first generate a random overlapping population of fragments encompassing that piece and to then "shotgun" clone these fragments into a vector. The resulting pool of recombinants is called a "library." These recombinants can be individually propagated, and the DNA sequence of the individual cloned inserts may then be determined. The DNA sequence obtained from individual cloned inserts can be combined to generate the DNA sequence of the entire segment of DNA.

A common vector for generating such libraries is M13 phage, a filamentous bacteriophage that infects *E. coli* to produce progeny phage particles harboring only one strand (the "plus" strand) of the viral genome. The genomes of filamentous *E. coli* phage consist of single-stranded circular DNAs of about 6,400 nucleotides. The products of the genes encoded in this DNA are involved in phage DNA replication, phage capsid synthesis, and phage assembly.

The single strand produced by the M13 phage is an ideal template for oligonucleotide-directed DNA sequencing using the Sanger chain termination method (for example, Heidecker, et al., *Gene*, 10:68, 1980) because the method depends on the annealing of a oligonucleotide primer to a single-strand template. By using the M13 phage as a vector for a segment of cloned DNA, the cloned DNA can be produced in the single-strand form attached to known flanking sequences capable of being used as targets for the oligonucleotide primers.

After a fragment of DNA has been inserted into the filamentous phage, it is important to be able to differentiate between phage that have a cloned insert and phage that do not. The discrimination of clones containing inserted foreign fragments from those that do not is generally done by means of a blue-white color selection (J. Messing, in *Methods of Enzymology* 101 (part C), Wu et al., Eds, Academic Press, N.Y., 1983). The color selection technique works because the inserted DNA interrupts a gene responsible for producing an enzyme that produces a colormetric reaction when a specific substrate is added.

The blue/white selection technique is an "indirect" cloning approach because all phage (whether recombinant or not) are propagated. This approach, although powerful and convenient, is nonetheless laborious, costly, variable in efficiency, and refractory to effective automation.

Waye, et al. discloses a direct selection technique for the filamentous phage M13 using the properties of the bacterial EcoK gene.

What is needed in the art of cloning is a filamentous phage vector system that provides direct selection due to the properties of a filamentous phage gene, such as gene X. Gene X is a filamentous phage gene involved in phage DNA replication.

SUMMARY OF THE INVENTION

One embodiment of the present invention is a vector comprising a filamentous phage sequence, wherein the sequence contains a first copy of gene X, which is defined hereafter. The vector also comprises a second copy of the gene X sequence downstream from a promoter capable of promoting transcription in a bacterial host. In a preferred form of the invention, the filamentous phage is M13 and the vector additionally comprises a restriction endonuclease site located in such a manner as to substantially inactivate the second gene X when a DNA sequence is inserted into the restriction site.

In another embodiment, the present invention is a method of isolating a recombinant filamentous phage vector comprising first inserting a foreign fragment of DNA into the restriction site of the above-described vector, wherein a mixture of recombinant and non-recombinant vectors is formed. The mixture is propagated in a host wherein the recombinant vectors are preferentially propagated. The recombinant vector is then isolated.

An object of the present invention is to provide a direct cloning method using filamentous phage.

Another object of the present invention is to provide a filamentous phage vector with a second copy of gene X.

It is an advantage of the present invention that the filamentous phage vector with an inserted fragment of foreign DNA will preferentially propagate as opposed to the filamentous phage vector without a foreign fragment insertion.

It is another advantage that the steps and reagents previously used in indirect selection techniques are eliminated, thus reducing time and cost and making the method of the present invention more amenable to automation.

Other objects, advantages and features of the present invention will become apparent after review of the specification, claims and drawings.

DESCRIPTION OF THE DRAWINGS

FIG. 1 is a schematic drawing of one embodiment of the vector of the present invention.

FIG. 2 is a diagram of the sequences (SEQ ID NO: 1) directly upstream from the second copy of gene X and the sequence of gene X in the FIG. 1 embodiment of the present invention.

DESCRIPTION OF THE INVENTION

1. In General

One aspect of the present invention is a vector that provides direct selection of recombinant vectors. By "direct" selection of recombinant vectors, we mean a system that preferentially allows recombinant vectors to proliferate. This invention provides direct (or "positive") selection of recombinant clones for the purpose of DNA sequencing by creating a filamentous phage vector containing an additional copy of the M13 gene X. Gene X is a filamentous phage gene involved in phage DNA replication.

A diagram of a typical vector of the present invention is shown in FIG. 1. (For clarity, some of the M13 genes have been eliminated from the diagram. The typical vector of the present inventor contains the entire M13 genome.) The direct selection capability of the vector is achieved by taking advantage of the "inhibitory" or "repression" activity of the gene X protein. This is accomplished by ligating an extra copy of filamentous phage gene X into a filamentous phage.

The gene X product is encoded by an M13 gene and is one of only three phage proteins needed for phage DNA replication. The relative placement of these M13 genes and the origin of replication are shown on the M13 genomic map depicted in FIG. 1.

The genome of a typical filamentous phage, M13, contains genes other than those diagrammed in FIG. 1. (For a review, see Model and Russel in *The Bacteriophage* VII, pp. 375–456, Ed. R. Calendar, N.Y., Plenum Press, 1988.) The genes are tightly packed but interrupted by an intergenic (IG) region between genes IV and II. The IG region contains the (+) and (−) origins of DNA replication, the packaging or morphogenetic signal, and the rho-dependent terminator. The 3'-end of gene I overlaps the 5'-end of gene IV. There is a small intergenic region between genes VIII and III which contains a rho-independent terminator and the promoter for gene III.

The M13 genes and the proteins encoded can be grouped into those that make up the virion (products of genes VIII, III, VI, VII, and IX), those required for DNA synthesis (genes II, V, and X), and those that serve a morphogenetic function (genes I and IV). Most mutations are lethal to M13, leaving very few "inessential" parts that can be replaced or interrupted by another DNA sequence. The IG region is believed to contain only two areas of inessential stretches of DNA which, if cloned into, would not render the phage defective.

One inessential region is located upstream of the (−) origin (approximately between nucleotides 5580 and 5610). This is where the gene X cistron of the version of the invention discussed in the Example is cloned in M13-100.

The other inessential region is located downstream of the (+) origin and before the start of gene II transcription. It is in this region (approximately between nucleotides 5820–5920) that the mp cloning system was developed. The intergenic region between genes VIII and III represents a potential region for cloning foreign DNA as long as its regulatory sequences are not disrupted. No other regions of the phage seem to be dispensable.

The gene X protein is 144 amino acid residues in length and is identical to the C-terminal third of the gene II protein. Translation initiation is at codon 300, AUG, of gene II. The gene X product is required for efficient accumulation of viral DNA export (Fulford and Model, *J. Mol. Biol.* 203:39–48, 1988). The gene X protein is a powerful inhibitor of phage-specific DNA synthesis in vivo and is thought to operate at the earliest stages of DNA replication, thus giving the protein a regulatory function without which the infected cell is incapable of accumulating progeny ssDNA particles. If over-produced, the resulting high levels of gene X protein blocks all phage-specific DNA synthesis (Fulford and Model, *J. Mol. Biol.* 203:49–62, 1988).

The vector of the present invention is designed to allow over-expression of an extra copy of gene X. In one embodiment of the present invention a copy of gene X and regulatory sequences are inserted into a dispensable portion of the intergenic (IG) region, near the origin (ori) of replication, as shown in FIG. 1. It is not necessary for the present invention that the extra copy of gene X be inserted at exactly the same locus as shown in FIG. 1 because there are other dispensable portions of the M13 genome as discussed above.

In the FIG. 1 embodiment of the present invention, high-level expression of the gene X product is driven by the strong bacteriophage T7 promoter and ribosome binding site (RBS) positioned upstream of the gene X initiation codon. (Our term for the combination of gene X and regulatory sequences is the "gene X cistron".) The T7 promoter is selectively recognized by phage T7 RNA polymerase and provides the basis of numerous expression systems for the overproduction of foreign proteins in *E. coli* (Studier, et al., *J. Mol. Biol.* 198:113–130 (1986); Studier, et al., *Meth. Enzymol.*, 185:60–89 (1990); U.S. Pat. No. 4,952,498). The promoter is obtainable by methods disclosed in the Examples below. We envision that other promoters and regulatory elements would be equally suitable for the present invention. These promoters and elements are specifically discussed below.

The entire cistron is preferably inserted in the opposite orientation as the endogenous gene X protein. This orientation is preferable because we envision that one using the present invention will most likely want to sequence the piece of inserted DNA and the T7 portion provides a convenient non-M13 region allowing primer-directed sequencing off the plus strand only when in this opposite orientation.

After the vector has been created, fragments of foreign DNA are inserted into a restriction site within the gene X cistron. Foreign DNA is typically fragmented into pieces of about 500–3000 base pairs before insertion into the vector. As described below, the DNA may be digested or partially digested with a "blunt-end" restriction endonuclease. A more common procedure for generating random overlapping fragments could be used here instead. These procedures involve sonicating the DNA and "polishing" the ends of the resulting fragments by filling in with DNA polymerase to help ensure that the majority of fragments are blunt-ended for higher efficiency of cloning. Alternatively, the DNA could be digested by a restriction endonuclease that creates fragments with "sticky" ends.

Selection of recombinant phage is achieved by inserting a foreign DNA fragment of interest into the new gene X cistron such that the expression of gene X is disrupted. Thus, the foreign DNA blocks the overexpression of gene X in cells which are producing T7 RNA polymerase. This insertion is accomplished by introducing a unique restriction endonuclease site within the gene X cistron, preferably within the gene X coding region itself so as to insure the direct inactivation of the gene X protein's inhibitory function. Alternatively, disruption of gene X expression can be accomplished by cloning into a restriction site placed at other positions within the promoter region, preferably between the T7 RBS and gene X initiation codon so as to help insure efficient disruption of both transcription and translation of gene X, simultaneously. The Example below demonstrates the latter method.

In our Examples below, we describe the insertion of an Eco RV site into the gene X cistron. An Eco RV site was chosen because it is a blunt-end cloning site which will accommodate the blunt-ends typically generated in the preparation of shotgun library fragments. However, many other blunt-end sites or sticky-end sites are equally suitable depending on what type of fragments one wishes to clone. It is convenient if the selected restriction site is unique in the vector. Otherwise, one will fragment the filamentous phage when trying to clone into the site.

The vector of FIG. 1 can be propagated to high titers in a strain of *E. coli* that does not express T7 RNA polymerase (eg. JM109). Because the *E. coli* does not produce T7 RNA polymerase, the T7 promoter placed upstream from the second copy of gene X cannot be activated. If one wishes to use a different promoter, the vector must be propagated in a host that does not activate the gene X.

Recombinants are selected by propagation in cells expressing T7 RNA polymerase (such as JM109(DE3) cells, Promega Corp., which contain a stably integrated IPTG-inducible T7 RNA Polymerase gene under lac promoter-operator control). If one wishes to use a different promoter, the cell type used to select recombinants must activate gene X expression. We call such cells "selection hosts".

Once the vectors have been propagated in the selection host, one typically selects those vectors that have survived. The surviving vectors are examined to determine whether they contain a foreign DNA fragment. Ideally, one would like to eliminate all the background parental vector. It is not necessary that the selection eliminate all of these vectors to be effective because one can examine the vectors individually for the foreign DNA fragment if the background of parental vectors is low enough so that the vast majority of the vectors are recombinants.

The recombinant plaques may show a reduced titer on the DE3 cells but can be grown back to high titer in any male *E. coli* strain not expressing T7 RNA polymerase such as JM109 when preparing supernatants for the preparation of DNA sequencing templates.

The level of basal expression of T7 RNA polymerase in JM109(DE3) cells is enough to obtain a 10,000-fold reduction in titer of the parental vector when compared to growth of JM109 cells. With IPTG-induction, another 400-fold reduction is observed, yielding a theoretical limit of parental vector background of 1 in 4 million for shotgun cloning.

2. Suitable Filamentous Phage

Although the examples below describe the preparation of a vector based on wild-type M13, other filamentous phage are also suitable for the present invention. Specific examples are phage f1 and fd. (Beck, et al., *Gene*, 16:35-58, 1981, Schaller, et al., *The Single-Stranded DNA Phages*, Denhardt, et al., Eds., pp. 139-163, Cold Spring Harbor Laboratory, Cold Spring Harbor, N.Y., 1978; Hill, et al., *J. Virol.*, 44:32-46, 1982; Van Wezenbeek, et al., *Gene*, 11:129-148, 1980.) These phage will also be inactivated by overexpression of the gene X protein. As their genomes are very similar to M13, the procedures described for creating the M13 phage are applicable to these filamentous phage.

3. Suitable Gene X Sequences

The M13 gene X has been described and sequenced (Beck, et al, supra). This gene can be obtained by PCR amplification of filamentous phage sequences (either M13 or another filamentous phage) with primers homologous to the 5' and 3' ends of the gene X sequence. FIG. 2 and SEQ ID NO:1 discloses a suitable gene X sequence.

Of course, other methods known to those skilled in the art are also suitable for obtaining gene X.

4. Other Variations

The present invention is not restricted to the use of the T7 phage promoter. T7 promoter is convenient because it is a well-characterized promoter, and it is easy to obtain cells which do and do not express the T7 RNA polymerase. However, other promoters are equally suitable.

In fact, promoters that are not as strong as the T7 promoters might be advantageous. A weaker promoter might be more easily disrupted by the insertion of a foreign gene.

Examples of suitable promoters are lac and tac promoters (See de Boer, et al., *Proc. Natl. Acad. Sci., U.S.A.*, 80:21 (1983); Amann, et al, *Gene* 25:167 (1983); Fulford and Model, *J. Mol. Biol.*, 203:49-62 (1988); Guarente, et al., *Cell*, 20:543-555 (1980) and, in general, Miller and Reznikoff, *The Operon*, Cold Spring Harbor Laboratory, Cold Spring Harbor, N.Y. (1978)).

A weaker RBS may be desirable instead of the very strong T7 RBS to obtain more efficient disruption of gene X translation. One might use either gene X's own RBS region found upstream of its naturally located start codon or, as is often done, construct a consensus RBS region as determined by the rules of Gold and Storm, for instance. (Gold, et al., *Methods in Enzymology*, 185:89-93, 1990).

It is only necessary to have a system in which the vector can be propagated in a host cell which does not activate the promoter and can be propagated in a host cell which will activate the promoter. Other examples of activation/inactivation systems include:

(1) *E. coli* hosts expressing the lac repressor (lacI or the over-expressed lac I$^Q$ gene)

As examples, the lac and tac promoters come equipped with the operator sequences that bind the lac repressor, thereby preventing transcription. Placing these promoters in front of gene X would allow for the gene's differential regulation in these hosts. The vector could be propagated in IacI$^Q$ strains such as JM109 or DH5αF'IQ and recombinants could be selected in the same strains where gene X expression is induced by the addition of IPTG (which inactivates the repressor).

(2) Hosts expressing suppressors of conditionally lethal mutants such as amber mutations For example, an amber mutation in the coding portion of the gene X cistron could be introduced such that its expression is impaired through premature termination of translation. The vector could be propagated in a sup$^-$ strain whereas recombinants could be selected in a sup$^+$ strain where the amber mutation would be suppressed allowing for gene X activation. There are numerous male Sup$^-$ and Sup$^+$ strains of *E. coli* available from ATCC. For example, the following strains are available from ATCC:

| SUP− | SUP+ |
|---|---|
| JM101 | JM103 |
| JM105 | JM107 |
| NF1829 | JM109 |
| LA6:F+r-m- | NM522 |
| RR1deltaM15 | R4 |
| K38 | DH5αF' |

The placement of the unique restriction site is not necessarily in the same position as in the Example below. This restriction site might easily be placed within the gene X itself or in other places in the promoter. In constructing the vector of the present invention, one first tests to confirm that the placement of the gene X is such that the insertion location of a foreign piece of DNA inactivates gene X. This can be done by a simple set of experiments. One would construct the vector with the restriction site in the desired location and attempt to insert a piece of DNA, for example, at such ratios of insert to vector that the insertion is sure to occur at a high percentage. The vectors are then placed in a selection host. One then examines the population of resulting vectors to determine whether or not gene X had been activated or inactivated. If a high percentage of the resulting vectors are recombinant, the gene X protein has been inactivated.

EXAMPLES

1. Construction of the M13-100 Vector

The M13-100 vector was constructed by ligation of a recombinant PCR fusion product into a unique Eco RV site which was previously inserted into wild-type M13 (called M13SPS1). Wild-type M13 is commercially obtainable, for example through ATCC. The Eco RV site was part of a polylinker, Bam H1-Eco RV-Eco R1, cloned by oligo-directed mutagenesis around position 5600 of the M13 intergenic region near the phage origin of replication.

The construction of the M13SPS1 vector was a two-step process. First, a single Eco RV site was introduced into WT M13 DNA by oligo-directed mutagenesis using the T7-GEN ™ in vitro Mutagenesis kit (U.S. Biochemical Corp.). The oligonucleotide was designed to introduce four new bases to M13 between bases 5605 and 5606 (by phage fd sequence numbering) and create a unique Eco RV site. This new phage was called M13RV. After being cut with Eco RV, a new oligonucleotide was blunt-end ligated into M13RV, thereby inactivating the Eco RV restriction site. This oligonucleotide contained a new Eco RV site flanked by Eco R1 and Bam H1 sites. It has the sequence shown in SEQ ID NO:2 and is cloned in the opposite orientation in M13SPS1 (The oligonucleotide also contains the "universal primer" sequence which is not pertinent here).

The PCR fusion product consisted of 2 fragments: (1) the bacteriophage T7 gene X promoter and RBS joined to (2) M13 gene X. Each portion was generated with specific primer pairs. The primer pairs for fragment 1 were complementary to the T7 promoter region in the plasmid pGEMEX-1 (Promega Corp., Madison, Wis.), which was used as the template for amplification. The primer pairs for fragment 2 anneal to wild-type M13, which was used as template. The right primer of 1 and left primer of 2 are complementary to each other through the T7 RBS region.

M13 gene X (335 bp including TAA) was PCR-amplified from WT M13 template ssDNA using primers described at SEQ ID NOs:3 and 4.

The T7 promoter region (100 bp) was PCR-amplified from WT M13 template ssDNA using primers described at SEQ ID NOs:5 and 6.

The M13 gene X and T7 promoter region PCR products were gel-purified by electro-elution from agarose gels and then fused together in another PCR amplification reaction containing both PCR products used as template and only primers T7L and XR. The final PCR fusion product is called the "gene X cistron". Both FIG. 2 and SEQ ID NO:1 show the DNA sequence of the fusion product consisting of the upstream region containing the T7 promoter, T7 RBS and Eco RV cloning site joined to the gene X coding sequence.

The gene X cistron fragment was blunt-end ligated into M13SPS1RF DNA cut with Eco RV.

The ligation reaction product was used to transform E. coli JM109 cells. Resulting plaques were grown in 1 ml liquid cultures for 8 hours. Cell pellets were extracted for analysis of RF DNA by restriction digestion with Eco R1 and Bam H1 which flank the insert. In the plaque isolate, M13-100, this new T7/gene X cistron was found to be cloned in the opposite orientation as the endogenous M13 gene X.

The RF DNA "minipreps" were screened for those having the correct insert by double-digesting with Eco R1 and Bam H1 because these restriction sites flank the Eco RV cloning site in the M13SPS1 vector. If cloned as a single copy, the T7/X fusion product should be released as a 450 bp fragment after digestion as judged by electrophoresis on an ethidium bromide stained agarose gel when run against standard markers of known size. M13-100 was isolated by this criteria. Orientation was first checked by performing double digests of Bam H1/Xba I and Eco R1/Xba I. (Xba I is a unique site asymmetrically located near the T7 promoter (see FIG. 2)). The entire gene X cistron sequence, orientation, and insert/vector junctions were also later confirmed by DNA sequencing using oligonucleotide primers complementary to M13 that lie outside the insert.

A high titer supernatant stock of M13-100 was prepared and titered on JM109 and JM109(DE3), the latter expressing (IPTG-inducible) T7 RNA polymerase. The results of such an experiment are shown in Table 1 which indicates, based on actual the levels of repression observed, that theoretical background levels of M13-100 when used as a shotgun cloning vehicle should approach 1:10,000 (basal) to 1:4 million (induced).

TABLE 1

| | Plaque-forming units per ml | | | Reduction | |
|---|---|---|---|---|---|
| | JM109 | JM109(DE3) -IPTG | +IPTG | − | + |
| M13SPS1 | $1.5 \times 10^{13}$ | $1.4 \times 10^{13}$ | $1.5 \times 10^{13}$ | 0 | 0 |
| M13-100 | $3 \times 10^{13}$ | $2 \times 10^9$ | ND | $1.5 \times 10^4$ | |
| | $7 \times 10^{12}$ | $1 \times 10^8$ | $1.6 \times 10^6$ | $7 \times 10^3$ | $4 \times 10^6$ |

2. Preparation of M13-100 RF DNA for Shotgun Cloning

To achieve high titers, the M13-100 phage was propagated in male E. coli cells not expressing T7 RNA polymerase. We used JM109 cells purchased from Promega Corp. Other E. coli strains have been used successfully to grow M13-100, including K38 and DH5αF'.

The circular, double-stranded RF (replicative form) DNA was extracted and purified directly from infected cell pellets. Standard protocols for phage infection and plasmid purification were used. (e.g., Sambrook, et al in *Molecular Cloning, A Laboratory Manual*, Chap. 4, Cold Spring Harbor Laboratory Press, N.Y.) Briefly, 100 ml of an early log culture of JM109 cells (A600=0.1 OD) was infected with M13-100 phage obtained from a high-titer supernatant stock ($10^{12-13}$ pfu/ml) at a multiplicity of infection (MOI)=1. The infection was carried out at 37° C. for 5-8 hours while shaking in an orbital incubator at 250 rpm. The cells were centrifuged at 5,000 rpm for 10 minutes and the supernatant decanted. This supernatant, if saved, served as a high titer stock of phage.

The cell pellet was then harvested and the RF DNA purified using the Qiagen plasmid purification kit (Qiagen, Inc.). This kit utilizes the well-known alkaline-lysis procedure of Birboim and Doly followed by a gravity flow ion-exchange column selective for supercoiled DNA. (It also effectively removed contaminating single-stranded M13 DNA).

Alternatively, one could use other kits available on the market or equilibrium centrifugation in CsCl-ethidium bromide density gradients.

After the propanol precipitation step, the DNA was resuspended in 200 ul of TE (10 mM Tris.HCl, 1 mM EDTA, pH 7.5) at a concentration of about 1 mg/ml.

For cloning, the DNA (10–20 ug) was linearized restriction endonuclease digestion with Eco RV according to the manufacturer's recommended conditions. The shortest incubation time (0.5–1.0 hr) and the least amount of enzyme (0.5 units/ug DNA) permitting digestion to near completion (as visualized on an agarose gel) is recommended for cutting the vector. This helps minimize the activity of trace amounts of exonucleases present in commercial enzyme preparations which, after vector religation, can ultimately lead to the generation of false positives by creating deletions around the cloning site (ie. into gene X).

The Eco RV-cut DNA was cleaned up first by electrophoresing on a low-melt agarose gel followed by eluting the sliced out band using the Magic TM PCR Prep DNA Purification System (Promega Corp.). The gel elution step helps remove trace amounts of contaminating digested chromosomal DNA fragments leading to false positives by insertion. The DNA recovered from this procedure was ready for the ligation step.

3. Preparation of Random DNA Insertion Fragments

As a test of a shotgun library construction using M13-100, we obtained from Dr. Richard ffrench-Constant (Dept. Entomology, U. WI) a purified plasmid subclone containing an 11.5 kb insert of Drosophila DNA encoding a portion of the gamma-aminobutyric acid (GABA) receptor gene. This fragment is part of a larger GABA cosmid clone of about 40 kb in length which represents a typical size for shotgun sequencing in M13. We prepared random insertion fragments using partial digestion with the two-cutter restriction endonuclease, CviJ1. This enzyme cuts DNA quasi-randomly between bases G and C within the sequence PuGCPy, generating blunt-end fragments. Fitzgerald, et al. *Nucleic Acids Research*, 20[14]:3753–3762, 1992. CviJ1 was obtained from J.Van Etten (U. Nebraska) and is not yet commercially available.

We cut 5–10 ug of the GABA DNA with CviJ1 and size-select fragments using either a Sephacryl-400 spin column (for fragments above 500 bp) or elution from low-melt agarose gels (above 1000 bp).

4. Ligation of Random GABA Fragments into the M13-100 Vector

The vector and GABA fragments were ligated in 20 ul reactions such that the molar ratio of inserts: vector is about 2:1, assuming an average size of fragments to be around 3000 bp (200 ng vector; 50 ng insert). Reactions were carried out overnight at 15° C. in 1× manufacturer's ligation buffer (New England Biolabs) using 2000 units of T4 DNA ligase (NEB). Control reactions containing just vector, plus and minus ligase, were also performed to determine ligation efficiencies and background due to vector religation. Ligation reactions were terminated by heating to 65° C. for 15 minutes. The ligation reaction itself can be thought of as a "shotgun library" before transformation and plating when stored at −20° C.

5. Transformation of E. coli with the GABA Library

For positive selection of recombinants, the ligation reactions were used to transform JM109(DE3) cells which express T7 RNA polymerase. Transformation of JM109 cells was sometimes done for comparison to observe levels of foreground and background repression. Transformation was carried out by electroporation using the Bio-Rad *E. Coli* Pulser. Briefly, one-tenth of the ligation reactions (2 ul or 20 ng DNA) were added to 40 ul of electrocompetent JM109(DE3) cells prepared according to Bio-Rad's protocol. After pulsing, 1 ml of media (2×YT) was immediately added and 100 ul was plated onto 85 mm LB plates in 3.5 ml top agar (0.75%) containing 100–200 ul of JM109 or JM109(DE3) fresh lawn cells (A600 around 1.0–2.0). Plaques were developed overnight at 37° C.

Electroporation was chosen for our experiments because of its high efficiency compared to other protocols. Typically, electroporation yields transformation efficiencies of $10^{10}$ pfu/ug DNA for plasmids but only $10^8$ for M13 RF DNA. Transformation efficiencies of M13 DNA are notoriously low no matter which cell strain or transformation protocol is used. Table 2, below, tabulates experimental results which indicate that a foreground (plaques with GABA inserts) to background (plaques without inserts) ratio of up to 450:1 is achievable with just basal level of T7 polymerase in the JM109(DE3) cells. It is envisioned that the level of background may vary between at least 0.1% and 1%, and will only ever be as good as the quality of the enzymes used to prepare the vector. The theoretical background limits discussed earlier are achieved once variables are eliminated and the efficiency of ligation approaches 100%.

Preliminary experiments examining the effects of elevated levels of T7 polymerase after IPTG-induction demonstrated a reduction in foreground, probably representing "toxic" over-expression of recombinant sequences, expressed T7/gene X-containing polycistronic message, or a combination of both (data not shown). It is hoped that this problem can eventually be cured by (1) moving the cloning site to somewhere inside gene X, and/or (2) changing to a weaker promoter/RBS expression system.

TABLE 2

| | Plaque forming units/200 ng DNA | | | |
|---|---|---|---|---|
| | EXPT 1 | | EXPT 2 | |
| | JM109 | JM109 DE3 | JM109 | JM109 DE3 |
| Uncut RF M13-100 | 3.2 × 10⁷ | 1,240 | 1.2 × 10⁷ | 2,800 |
| M13-100 + Eco RV | 6,400 | 0 | 1,100 | 0 |
| M13-100 + Eco RV + Ligase | 240,000 | 200 | 452,000 | 30 |
| M13-100 + Eco RV + Ligase + GABA | 259,000 | 51,000 | 519,000 | 13,420 |

6. Insert Sizing and Sequencing

Cell pellets of recombinant plaques (from a >500 pb size-selected library) were grown to high titer in 1 ml JM109 liquid cultures and their RF forms analyzed by restriction digestion with Bam H1 and Eco R1 to estimate GABA insert sizes. An expected random size distribution of insert sizes ranging from 200 to 3500 bp was observed on agarose gels. Single-stranded DNA in the supernatants of these recombinant plaques were extracted and purified with Pharmacia Sephaglass and used as templates for Sanger DNA sequencing by $^{35}$S-dATP incorporation with Sequenase (U.S. Biochemicals). The 3'OH of the oligonucleotide used as primer maps to −35 bp from the Eco RV cleavage site. The sequencing reactions were run on an 8M urea-5% acrylamide gel and exposed to X-ray film for 16 hours.

A number of changes and modifications to the present invention will be apparent to those skilled in the art without departing from the spirit and scope of the invention. For instance, "gene X" as used herein is intended to cover the specific M13 gene X sequence disclosed herein as well as functionally equivalent sequences. Therefore, the invention is only to be limited by the claims.

---

We claim
1. A vector comprising
   a filamentous phage sequence, wherein the sequence contains a first copy of gene X and wherein the sequence contains all sequences necessary to enable the phage to propogate, and wherein the filamentous phage is selected from the group consisting of M13, fd and f1, and
   a second copy of the gene X sequence downstream from a promoter capable of promoting transcription of gene X in a bacterial host,
   wherein the second copy of gene X is between nucleotide 5580 and 5610 or between nucleotide 5820 and 5920 of the filamentous phage sequence.

2. The vector of claim 1 wherein the filamentous phage is M13.

3. The vector of claim 1 wherein the promoter is the phage T7 promoter.

4. The vector of claim 1 additionally comprising a restriction endonuclease site located in such a manner as to substantially inactivate the second copy of gene X when a DNA sequence is inserted into the restriction site.

5. The vector of claim 4 wherein the restriction endonuclease site is within the second copy of gene X.

6. The vector of claim 4 wherein the restriction site is between the ribosome binding site and the translation initiation codon of the second copy of gene X.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 451 base pairs
        ( B ) TYPE: nucleic acid
        ( C ) STRANDEDNESS: double
        ( D ) TOPOLOGY: unknown ( i i ) MOLECULE TYPE: RNA (genomic)

( x i ) SEQUENCE DESCRIPTION: SEQ ID NO:1:

```
GGATCCGATA  GATCTCGACC  CGCGAAATTA  ATACGACTCA  CTATAGGGAG  ACCACAACGG    60
TTTCCCTCTA  GAAATAATTT  TGTTTAACTT  TAAGAAGGAG  ATATCATATG  AATATTTATG   120
ACGATTCCGC  AGTATTGACG  CTATCCAGTC  TAAACATTTT  ACTATTACCC  CCTCTGGCAA   180
AACTTCTTTT  GCAAAAGCCT  CTCGCTATTT  TGGTTTTTAT  CGTCGTCTGG  TAAACGAGGG   240
TTATGATAGT  GTTGCTCTTA  CTATGCCTCG  TAATTCCTTT  TGGCGTTATG  TATCTGCATT   300
AGTTGAATGT  GGTATTCCTA  AATCTCAACT  GATGAATCTT  TCTACCTGTA  ATAATGTTGT   360
TCCGTTAGTT  CGTTTATTA   ACGTAGATTT  TTCTTCCCAA  CGTCCTGACT  GGTATAATGA   420
GCCAGTTCTT  AAAATCGCAT  AAATCGAATT  C                                   451
```

( 2 ) INFORMATION FOR SEQ ID NO:2:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA to scRNA ( x i ) SEQUENCE DESCRIPTION: SEQ ID NO:2:

```
TGTAAAACGA  CGGCCAGTAA  TGAAAAAGA   ATAGATAAGA  ATTCGATATC  GGATCCC       57
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AAGGAGATAT  CATATGAATA  TTTATGACGA  TTCC                                  34
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:4:

TTATGCGATT TTAAGAACTG G    21

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGATCTCGAT CCCGCAA    17

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CATATGATAT CTCCTTCTTA AAG    23